United States Patent
Silver

[11] 3,945,381
[45] Mar. 23, 1976

[54] EYE DROP DISPENSER AND CUP

[75] Inventor: Jules Silver, Norwich, Conn.

[73] Assignee: Silver Industries, Inc., Norwich, Conn.

[22] Filed: Oct. 18, 1974

[21] Appl. No.: 516,092

[52] U.S. Cl. ............... 128/249; 222/546; 222/551; 222/562
[51] Int. Cl.$^2$......................................... A61H 33/04
[58] Field of Search .......... 222/205, 420, 545, 546, 222/551, 562; 128/249, 233

[56] References Cited
UNITED STATES PATENTS

| | | | |
|---|---|---|---|
| 1,370,665 | 3/1921 | Moore | 222/546 X |
| 1,680,994 | 8/1928 | Karpe | 222/546 X |
| 2,585,264 | 2/1952 | Mock | 128/249 |
| 2,756,530 | 7/1956 | Nelson | 222/205 X |
| 3,016,898 | 1/1962 | Erwin | 128/249 |
| 3,121,511 | 2/1964 | Whitehead | 128/249 X |
| 3,465,923 | 9/1969 | Konefal | 222/546 X |
| 3,767,088 | 10/1973 | Deessen | 222/205 |
| 3,872,865 | 3/1975 | Casey | 222/420 |

Primary Examiner—Robert B. Reeves
Assistant Examiner—Frederick R. Handren

[57] ABSTRACT

An eye drop dispenser consisting of a flexible container having an open neck defining a nozzle through which liquid is dispensed, includes an eye drop cup removably secured to the neck of the dispenser and having a free edge for engaging the eyelids of a person using the dispenser, in order to hold the eyelids against movement during application of eye drops to the eye. The cup is secured to the neck of the dispenser through an opening formed in one end thereof, which opening receives and engages the neck of the container with a portion of the neck extending through the opening and into the cup. A cover is provided for the cup and container, which cover has a top portion and an integral elongated stem. The top portion of the cover overlies the free edge of the cup to close the open end of the cup and the elongated stem portion of the cover extends into the cup and includes means for operatively engaging and closing the neck or nozzle of the container so that the cover will simultaneously close both the dispenser nozzle and the opened end of the cup.

12 Claims, 5 Drawing Figures

EYE DROP DISPENSER AND CUP

The present invention relates to liquid dispensers, and more particularly to a dispenser which is adapted to apply eye drop solutions or medications to the eye.

Numerous devices have previously been proposed by which a person can apply eye drops or medicines into the eye without assistance. Such devices range from the well known glass eye wash cup, to more recently developed applicator bottles having nose bridges for supporting the applicator bottle in a fixed position with respect to the eye.

Where an eye wash cup type device is used, the eye wash liquid is usually poured into the cup and the cup is then applied to the eye. This arrangement is not entirely satisfactory in that the possibility exists of spillage of the eye wash liquid or medicine during pouring, and the inability to accurately meter the amount of liquid applied to the eye. In addition, the eye drop cup, being a separate article from the container, may be lost or misplaced so that it is unavailable when needed.

On the other hand, the more recently proposed devices which consist of squeeze bottles with dispensing tips, with or without a nose bridge guide arrangement, are inherently dangerous in that the narrow dispenser tip of these type of arrangements can damage the eye if the user causes the tip to contact the eye. Moreover such devices are difficult to use since most people have a reflexive tendency to blink the eyelids when the eye drops are being inserted because of the reflexive fear of damaging the eye by contact with the dispenser tip. As a result, the liquid is not properly applied to the eye and the solution is wasted. Moreover it is difficult for a person in applying the eye drops to his own eye to properly locate the tip of the nozzle with respect to the eye so that the drops from the nozzle fall onto the eye rather than on the outside of the eyelid.

Accordingly, it is an object of the present invention to provide an eye drop dispenser which has the advantages of conventional eye drop cups in maintaining the eyelid opened during application of an eye drop solution, and which also has the advantage of having the dispenser cup directly connected to the container for the solution.

Yet another object of the present invention is to provide a combined solution dispenser and eye drop cup therefor, which can be used to conveniently apply the eye drop solution to the eye, while maintaining the eyelids of the user open.

Another object of the present invention is to provide an eye drop cup for use with a dispenser container in combination with a cover that will simultaneously seal the cup and the container to protect both from dirt or other contaminants and/or loss of liquid from the container.

Another object of the invention is to provide a dispenser device which will prevent accidental damage to the eye from contact with a dispenser tip and which will also eliminate wastage of the eye drop solution as a result of misdirected drops.

Another object of the present invention is to provide an eye drop cup in combination with a dispensing container which will hold the eyelid in an open position while the drops or medicine are inserted, and which can remain mounted on and sealed to the container for storage.

Another object of the present invention is to provide an eye drop dispensing device which will, in combination with a nozzle tipped dispensing container, direct the nozzle of the tip over the center of the eye while simultaneously holding the eyelids open.

Another object of the present invention is to provide an eye drop dispensing device which will properly direct eye drops from the nozzle of a container, while keeping the nozzle in spaced relation to the eyeball.

In accordance with one aspect of the present invention, an eye drop dispenser is provided which utilizes a flexible squeezable eye drop solution container having an elongated neck defining a nozzle through which drops of solution can be dispensed. This container is used in conjunction with an eye drop cup having an opened end portion which defines a free peripheral edge and a second end portion which has an opening therein that receives and surrounds the neck of the container in an operative engagement which removably secures the cup to the neck. With this arrangement the free edge of the cup can be placed against the eyelids of the user and then, after tilting of the head, the bottle or container can be squeezed to dispense individual droplets directly to the eye. The free edge of the cup will hold the eyelids open, preventing the user from blinking or shutting the eye completely. The cup is dimensioned with respect to the nozzle of the container so that the free end of the nozzle is located within the container a distance below the free end so that when the free edge of the cup is placed against the eyelid the nozzle end will be held in spaced relation from the eye thereby avoiding possible contact between the eye and the nozzle.

The cup is provided with a cover arrangement which is adapted to close the cup while it is on the container, and also to close the nozzle and seal it against possible leakage. By the provision of this cover arrangement, the cup can be kept on the dispenser at all times.

The above, and other objects, features and advantages of this invention, will be apparent in the following detailed description of an illustrative embodiment thereof, which is to be read in connection with the accompanying drawings, wherein.

Figure 1:
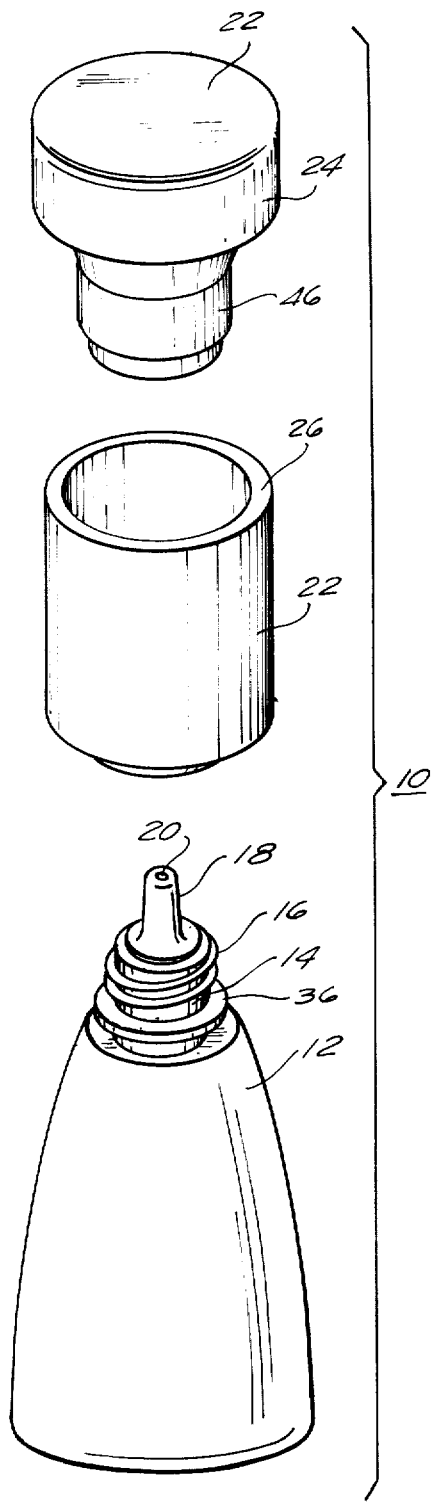
FIG. 1 is an exploded perspective view of a dispenser, cup and cover combination constructed in accordance with the present invention.

Referring now to the drawing in detail, and initially to FIG. 1 thereof, it will be seen that an eye drop dispenser assembly 10, constructed in accordance with the present invention, includes a flexible container 12 of conventional construction containing a conventional eye drop solution or medicine. The container includes an integral neck 14 which has a threaded portion 16 adapted to threadably engage a conventional threaded cap (not shown in FIG. 1) for closing the nozzle portion 18 of the neck. Nozzle 18 is provided with an open end 20, in the conventional manner, through which individual drops of solution can be dispensed upon squeezing of the flexible bottle 12.

It is to be understood that although a specific neck construction for the bottle 12 is illustrated in the drawing using a threaded neck portion 16, other neck constructions for the bottle 12 can be utilized, for example, a snap fit or bayonet lock rather than the threaded arrangement 16.

Dispenser 10 also includes an eye drop cup 22 which is adapted to be secured to the neck 14 of bottle 12, and a cover 24 for the cup which will substantially simultaneously close the cup and seal the nozzle 18 when the dispenser is not in use. In addition, the cover serves to securely retain the cup on the container 12 when it is not in use so that the cup is not inadvertently misplaced.

Figure 2:
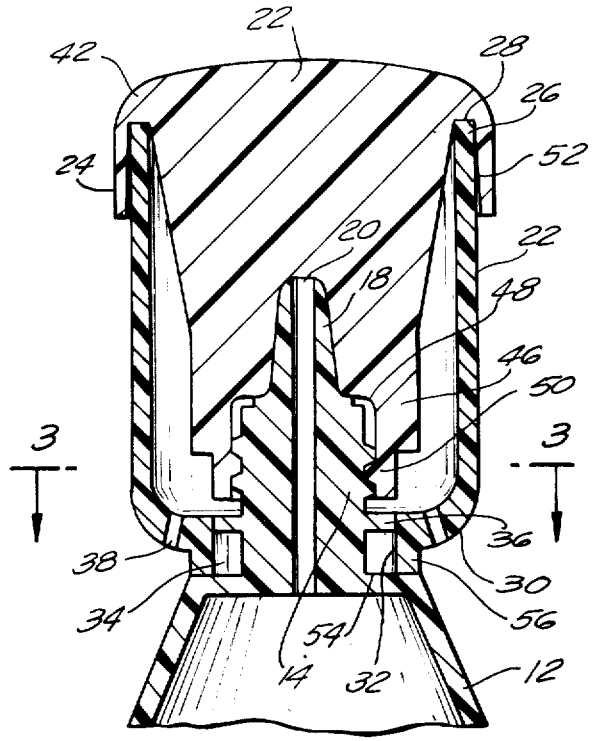
FIG. 2 is a sectional view of the upper end portion of the container, the cup and the cover illustrated in FIG. 1.
Figure 3:
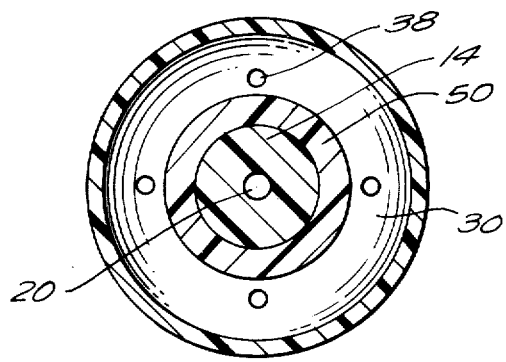
FIG. 3 is a plan view, in section, taken along lines 3—3 of FIG. 2.

Referring more specifically to FIGS. 2 and 3 of the drawing, it is seen that the cup 22 is a generally cylindrical member having an open upper end 26 which provides an annular free edge 28. The opposite end of the cup has a curved bottom wall 30 in which a generally cylindrical bore 32 is formed that provides a cylindrical side wall 34 in the bottom of the cup. This side wall has an internal diameter which is substantially equal to the maximum external diameter of the neck 14 of bottle 12. In the illustrative embodiment of the invention the bottle 12 has an annular flange 36 formed on the neck 14 which engages the cylindrical ball 34 of the cup 22 in a friction fit to securely retain the cup on the neck. Of course it will be appreciated that the particular configuration of the container neck and the cross section of the bore 32 can be changed as necessary. Thus if the neck has a square or rectangular configuration the bore 32 would have a similar configuration in order to produce the required friction fit for retaining the cup on the neck. As an alternative, other connection means can be used; for example if the neck 14 is threaded throughout its entire extent, the internal surface of the bore 32 can be threaded in a complementary manner, to threadably secure the cup to the bottle neck.

In any case, the height of the bore 32 is selected to be substantially less than the total height of the neck 14 of the bottle so that a major portion of the neck 14 extends through the opening 32 into the interior of cup 22. Preferably the height of the cup 22 is selected so that when it is secured to the neck 14, in the manner described above, the open end 20 of the nozzle 18 is located substantially below the free edge 28 of the cup.

Figure 4:
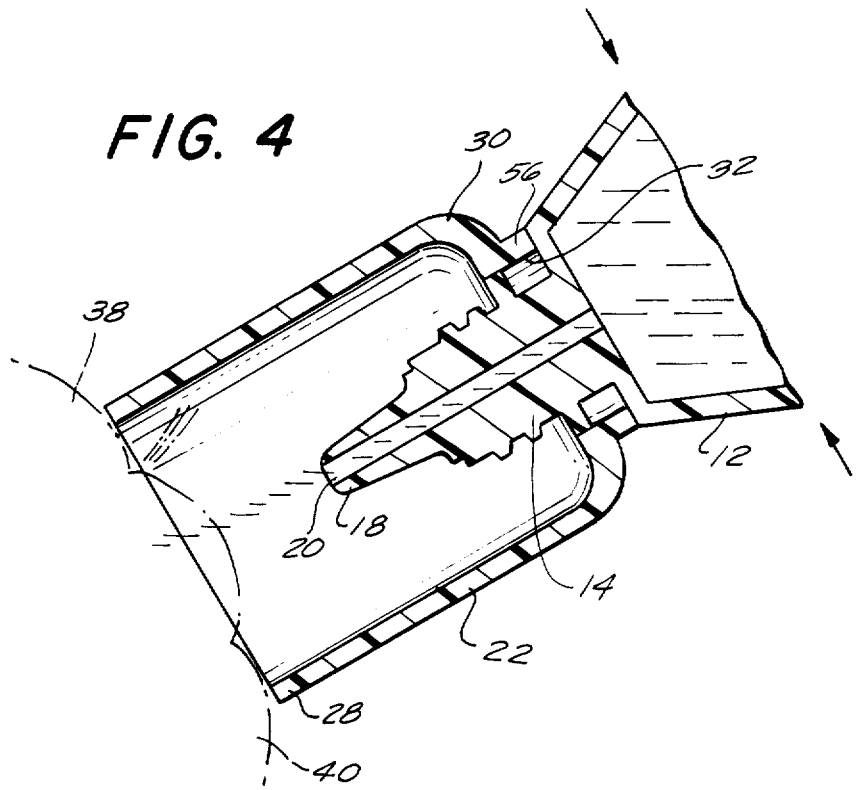
FIG. 4 is a sectional view similar to FIG. 2, but with the cover removed and showing the manner in which the liquid solution is applied to the eye with the construction of the present invention.

With the cup 22 secured to container 12 in this manner, the cup can be used to apply liquid eye drops or medicine to the eye of the user, in the manner illustrated in FIG. 4. As seen therein, the user places the edge 28 of the cup 22 against the upper and lower eyelids 38, 40, tilts the head rearwardly, and then squeezes the flexible container 12 in order to dispense the liquid solution through the nozzle 18. In this manner, the annular edge 28 of cup 22 holds the eyelids in the open position, preventing the user from blinking, and allowing the liquid to drop directly onto the eye. At the same time, the end of the nozzle 18 is held in spaced relation from the eye so that the eye can not be damaged by contact with the end of the nozzle 18.

Cover 24 serves to close the open end 26 of cup 22 and the end 20 of nozzle 18 when the dispenser is not in use. As seen in FIG. 2 the cover 24 is formed as a one piece member having a top portion 42 and an elongated stem portion 44. The lower end 46 of stem 44 is provided with a recess 48 which is adapted to receive the end of the nozzle 18 and a portion of the neck 14. Where the neck 14 has a threaded exterior surface, the recess 48 is provided with a complementary thread 50, so that the cover can be threadably engaged with the nozzle.

Cover 24 also includes an annular recess or well 52 formed therein on the lower surface of top 42. As seen in FIG. 2, this recess is adapted to receive the upper edge 28 of the cup 22 when the cover is secured to the container neck 14. In this manner, the cover simultaneously closes the upper end of cup 22 and the nozzle 18. In addition, it will be appreciated that the cover acts with the nozzle 14 and container 12 to in effect clamp the cup in a fixed position on the bottle 12, between the recess 52 and the shoulder 54 of the bottle 12 on which the end 56 of the cup rests. Thus the cup 22 can not be inadvertently removed from the container 12 when the device is not in use. This arrangement also avoids the need for a positive locking engagement between the cup and the container; thereby reducing the cost involved in manufacturing the dispenser.

Although it is intended that the cover 24 be used with the cup 22 in the manner described above, to close the end of the container 12, it will be apparent that should the user not desire to utilize the cup 22, the cup can be removed from the container 12, and the cover 24 can then be used simply for the purpose for closing the end of the container, without the need for any other auxiliary or separate cover or closure therefor.

If desired, the base 30 of cup 22 can be provided with one or more openings 58 formed therein which provide drainage holes for solution which may drip into the cup during application of the solution to the eye. These holes also act as air vents to prevent build up of air in the cup during use of the container and also to prevent the formation of a vacuum in the cup should the user tightly apply the edge 28 of the cup to the eye during application of the eye drops.

Figure 5:
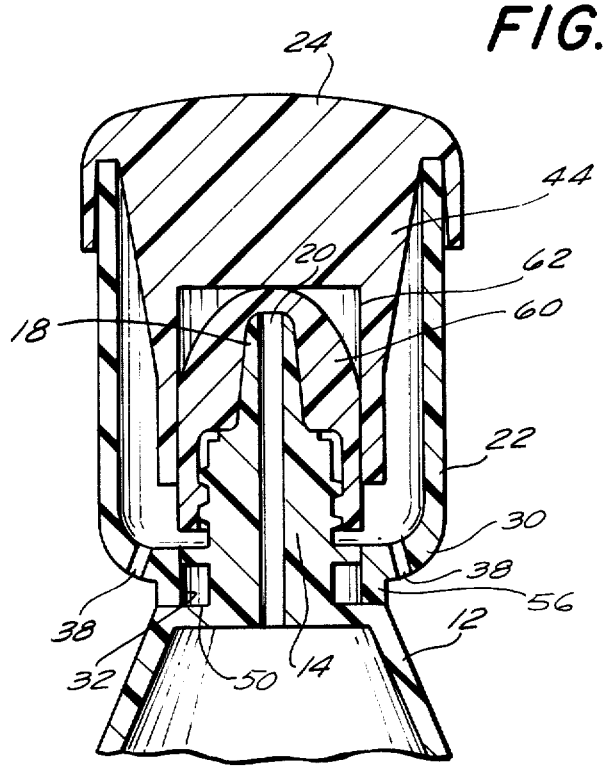
FIG. 5 is a sectional view similar to FIG. 2, but showing another embodiment of the invention.

Another embodiment of the invention is illustrated in FIG. 5. As seen therein the container 12 and cup 22 have the identical construction as that of the container and cup illustrated in FIG. 2. In this embodiment however the cover 24 has a slightly modified configuration in order to accommodate the cover 60 which is normally provided with commercially available eye drop containers. More specifically, the cup cover 24 is provided with a recess 62 formed in its stem 44, which recess is adapted to frictionally engage the conventional cover 60 of the eye drop container. With this arrangement, the cup and cover combination can be sold as a separate article of commerce for use with commercially available eye drop containers. As is well known such containers usually are sold with a cylindrical type cover or cap (i.e., the cover 60). By providing the cover 24 with a recess 62 therein, the commercial cap 60 can be inserted in the recess and frictionally held therein. In this manner, the commercial cap 60 of the container, as sold by the eye drop manufacturer, is used with the cover 24 in order to form the connection between the cover 24 and the neck 14 of the bottle. When the cover 24 is rotated to remove it from the bottle, the friction fit between the cap 60 and the recess 62 of cover 24 will cause the cap 60 to remain in the cover 24 and be removed therewith. Of course covers 24 can be provided with a variety of different shaped recesses 62 in order to accommodate the different commercially available caps used on eye drop solutions presently sold in the market.

The cut 22 and cover 24 of the dispenser devices described above can be formed of any suitable materials. Preferably, these elements are formed from a hard plastic material, but they may also be formed from glass, metal or a ceramic material.

By the construction of this dispenser of the present invention it will be appreciated that a convenient means for applying eye drops to the eye is provided which will simultaneously hold the eyelids open, against the tendency of the user to blink, while positioning the nozzle of the eye drop container above the center of the eye for direct application of the drops to the eye. At the same time, the end of the nozzle is held in a spaced relation (preferably ⅜ inch) from the edge of the cup so as to make it impossible for the tip of the nozzle to come into contact with the eye, thereby eliminating the danger of accidental damage to the eye or discomfort to the user. Moreover, the closure or cover 24 for the device serves several functions in that it simultaneously can close the nozzle of the container, to prevent leakage when it is not in use, while it also closes the end of the cup. By closing the end of the cup, the interior of the cup is protected from dirt or other contaminants which would enter the cup during storage. Such contaminants could possibly enter the eye when the cup was used, if the cup is not covered. Thus a more sanitary eye cup arrangement is provided. In addition, the cover serves to hold the cup on the container during storage so that the cup cannot be inadvertently misplaced and is available for use when necessary.

Although illustrative embodiments of the present invention have been described herein with reference to the accompanying drawings, it is to be understood that the invention is not limited to those precise embodiments, and that various changes and modifications may be effected therein by one skilled in the art without departing from the scope or spirit of this invention.

What is claimed is:

1. An eye drop dispenser and cover for use with a container for eye drop liquid having an open neck through which the liquid is dispensed, comprising, a cup having a first open end portion defining a generally circular free edge for engaging the eyelids of a person and a second opposite end portion having an opening therein for receiving and engaging the neck of the container with a portion of the neck of the container extending through said opening and into the cup; and a cover having a top portion overlying the entire free of said cup for completely closing said first open end thereof and an elongated stem portion extending into said cup and including means for operatively engaging and simultaneously closing the neck portion of the container; whereby said cover simultaneously closes the container and the entire open end of said cup; said stem portion of said cover including a free end portion and said means including a recess formed in said free end portion for receiving the neck of the container; said cup having a cylindrical bore formed therein defining said opening in its second end portion; said bore forming an annular wall in the cup having a cross section substantially complementary to at least a portion of the container neck for frictionally receiving the container neck therein.

2. The dispenser and cover as defined in claim 1 wherein said top portion of the cover has a well formed therein for receiving said free edge of the cup to close said cup.

3. The dispenser and cover as defined in claim 1 wherein said cup has at least one hole formed therein adjacent its second end portion for draining liquid spilled in the cup.

4. An eye drop dispenser and cover for use with a container for eye drop liquid having an open neck through which liquid is dispensed, comprising a cup having a first open end portion defining a free edge for engaging the eyelids of a person and a second opposite end portion having an opening therein for receiving and engaging the neck of the container with a portion of the neck of the container extending through said opening and into the cup; and a cover having a top portion overlying the free edge of said cup for closing said first open thereof and an elongated stem portion extending into said cup and including means for operatively engaging and closing the neck portion of the container; said stem portion of the cover having a free end portion and said means including a recess formed in said free end portion for receiving the neck of the container; and said neck of the container being threaded and said opening in said cup receiving said neck therein with at least a portion of the threads on said neck extending into the cup, said means in the stem of the cover including threads formed in said recess for threadably engaging said neck; whereby said cover simultaneously closes the container and the open end of the cup; said cup having a cylindrical bore formed therein defining said opening in its second end portion; said bore forming an annular wall in the cup having a cross section substantially complementary to at least a portion of the container neck for frictionally receiving the container neck therein.

5. An eye drop dispenser and cover for use with a container for eye drop liquid having an open neck through which liquid is dispensed, comprising a cup having a first open end portion defining a free edge for engaging the eyelids of a person and a second opposite end portion having an opening therein for receiving and engaging the neck of the container with a portion of the neck of the container extending through said opening and into the cup; and a cover having a top portion overlying the free edge of said cup for closing said first open end thereof and an elongated stem portion extending into said cup and including a free end portion having a recess formed therein; said neck of said container including a separate cap for closing its open neck; said recess in the stem portion of said cover being dimensioned to frictionally retain said cap therein for closing the open neck of the container when the cup is placed on said neck thereby to simultaneously close the container neck and the cap.

6. An eye drop dispenser comprising, in combination, a container for eye drop liquid having an open elongated neck defining an eye drop dispensing nozzle; a cup having a first open end defining a free circular peripheral edge and a second end portion having an opening therein receiving and surrounding said neck in operative engagement removably securing the cup to the neck, said neck extending through said opening to a position within the cup below the free edge thereof; said free edge of the cup being adapted to engage both eyelids of the user of the dispenser to prevent movement of the eyelids during placement of eye drops in the eye, and a cover for said cup and nozzle including a top portion overlying the entire free edge of the cup to completely close the first open end thereof and a stem portion extending into said cup and including means for simultaneously operatively engaging and closing said open neck of the container to prevent discharge of liquid from the container when the dispenser is not in use while simultaneously completely closing said cup to prevent contamination thereof; said stem portion of said cover including a free end portion and said means including a recess formed in said free end portion for receiving the neck of the container; said cup having a generally cylindrical configuration and a cylindrical bore formed therein defining the opening in its second end portion; said bore forming an annular wall on the cup having a cross section substantially complementary to at least a portion of the container neck for frictionally receiving the container therein.

7. The dispenser as defined in claim 6 wherein said top portion of said cover has an annular groove formed therein opening towards said cup for receiving the free edge of the cup when the cover is secured to the neck of the container.

8. The dispenser as defined in claim 7 wherein said cup has at least one hole formed therein adjacent its second end portion for draining liquid spilled in the cup.

9. An eye drop dispenser comprising, in combination, a container for eye drop liquid having an open elongated neck defining an eye drop dispensing nozzle; a cup having a first open end defining a free peripheral edge and a second end portion having an opening therein receiving and surrounding said neck in operative engagement removably securing the cup to the neck, said neck extending through said opening to a position within the cup below the free edge thereof; said free edge of the cup being adapted to engage both eyelids of the user of the dispenser to prevent movement of the eyelids during placement of eye drops in the eye, and a cover for said cup and nozzle including a top portion overlying the free edge of the cup to close the first open end thereof and a stem portion extending into said cup and including means for operatively engaging and closing said open neck of the container to prevent discharge of liquid from the container when the dispenser is not in use; said neck of said container including a separate cap for closing its open neck; said stem portion of the cover having a free end portion including a recess formed therein; said recess in the stem portion of said cover being dimensioned to frictionally retain said cap therein for closing the open neck of the container when the cup is placed on said neck thereby to simultaneously close the container neck and the cup.

10. The dispenser as defined in claim 9 wherein the cup has a generally cylindrical configuration and a cylindrical bore formed therein defining the opening in its second end portion; said bore forming an annular wall in the cup having a cross section substantially complementary to at least a portion of the container neck for frictionally receiving the container neck therein.

11. The dispenser as defined in claim 10 wherein said top portion of said cover has an annular groove formed therein opening toward said cup for receiving the free edge of the cup when the cover is secured to the neck of the container.

12. The dispenser as defined in claim 11 wherein said cup has at least one hole formed therein adjacent its second end portion for draining liquid spilled in the cup.

* * * * *